US 9,536,051 B1

(12) United States Patent
Kabir

(10) Patent No.: US 9,536,051 B1
(45) Date of Patent: Jan. 3, 2017

(54) HIGH PROBABILITY DIFFERENTIAL DIAGNOSES GENERATOR

(71) Applicant: Azad Alamgir Kabir, Slidess, LA (US)

(72) Inventor: Azad Alamgir Kabir, Slidess, LA (US)

(*) Notice: Subject to any disclaimer, the term of this patent is extended or adjusted under 35 U.S.C. 154(b) by 398 days.

(21) Appl. No.: 13/948,246

(22) Filed: Jul. 23, 2013

Related U.S. Application Data

(60) Provisional application No. 61/675,779, filed on Jul. 25, 2012.

(51) Int. Cl.
G06Q 10/00 (2012.01)
G06Q 50/00 (2012.01)
G06F 19/00 (2011.01)

(52) U.S. Cl.
CPC ......... G06F 19/3443 (2013.01); G06F 19/345 (2013.01)

(58) Field of Classification Search
CPC . G06F 17/3071; G06F 19/3443; G06F 19/345
USPC .......................................................... 707/737
See application file for complete search history.

(56) References Cited

U.S. PATENT DOCUMENTS

| 6,468,210 | B1* | 10/2002 | Iliff ........................ G06Q 50/22 128/904 |
| 6,754,655 | B1* | 6/2004 | Segal ..................... G06F 17/278 |
| 2002/0029157 | A1* | 3/2002 | Marchosky ........... G06F 19/322 705/3 |
| 2004/0153338 | A1* | 8/2004 | Kim ...................... G06F 19/322 705/2 |
| 2005/0131738 | A1* | 6/2005 | Morris .................. G06F 19/322 705/2 |
| 2006/0241978 | A1* | 10/2006 | Yoshii .................... G06Q 50/24 705/3 |
| 2012/0182291 | A1* | 7/2012 | Rawat ..................... G06T 17/00 345/419 |

* cited by examiner

Primary Examiner — Marc Somers
(74) Attorney, Agent, or Firm — Andrew Vicknair

(57) ABSTRACT

A method for performing an automated medical diagnosis of a patient based upon a patient's signs/symptoms/findings which are input by a user/heath care provider and then further analyzed to then output a listing of high probability differential diagnoses/diseases and a low probability differential diagnoses/diseases that the patient may have. This analysis assists health care providers in providing a fast and early indication of potential conditions based upon an analysis of a patient's signs/symptoms/findings.

4 Claims, 9 Drawing Sheets

HIGH PROBABILITY DIFFERENTIAL DIAGNOSES GENERATOR

CROSS REFERENCE TO RELATED APPLICATIONS

This application claims the benefit of U.S. provisional application Ser. No. 61/675,779 filed on Jul. 25, 2012.

TECHNICAL FIELD

The present invention relates, in general to automated diagnoses tools and, more particularly, to a high probability differential diagnoses generator to be used during patient care by a health care provider.

BACKGROUND OF INVENTION

The diagnostic thinking is defined as the process of hypothesis generation and testing. Therefore, the hypotheses generated at the beginning of a physician-patient encounter usually frames and structures the diagnosis, modulating its efficiency and accuracy. The initial hypotheses, although it may be modified by subsequent data, guides the physician's inquiry. The patient interview naturally elicits one or more hypotheses from the beginning. Sometimes a hypothesis is formulated even before the patient interview. This "working hypothesis" constrains not only the rest of the interview, but any subsequent hypotheses generation—which of course must also be tested.

Sometimes, physicians generate a diagnostic hypothesis early in the encounter. In fact, some physicians develop a working hypotheses during the first 50 seconds of a patient consultation. Some studies indicate that physicians form diagnostic hypotheses extremely early in the clinical encounter, and that the mean number of hypotheses under consideration at any time is between two and four.

Since the early generation of hypotheses is, and should be, the rule rather than the exception, it follows that one of the early hypotheses should have a reasonably high probability of being correct, to justify the elaborate system of history taking, physical examination, and the like.

In fact, focusing on an incorrect hypothesis and not considering alternative diagnoses is one of the major causes of diagnostic error. Under basic rules of diagnostic reasoning, within a minutes of a patient encounter (preferably with in 1-2 minutes), a health care provider, namely a physician and/or nurse, should generate at least 2-4 epidemiology-based hypotheses (i.e. rank-ordered hypotheses based on age-sex distribution of disease condition). Differential diagnosis should be heterogeneous or diverse. Diagnostic efficiency and accuracy depends on the quality of the hypotheses generated (i.e. how well the presumed differential diagnoses fits patient signs, symptoms and clinical findings). Experienced physicians usually formulate hypotheses and diagnostic plans very quickly, and the quality of their hypotheses is much better compared to that of novice physicians. Novice physicians often do not know how to generate appropriate hypotheses, they struggle to develop a diagnostic plan, and they have difficulty in establishing diagnostic possibilities from the collection of patient data.

The rank ordering of the generated hypotheses is also very important for effective diagnostic decision making. This rank ordering primarily depends on the epidemiological distribution of disease (determined by patient's age, sex, and clinical characteristics). Expert physicians will likely have an advantage over novices in term of rank ordering differential diagnoses as they learn over the years the distribution of diseases via clinical practice.

Currently, there are books that list all possible disease conditions a patient can have if a single sign or symptom or clinical finding is present. But every disease is related to multiple signs or symptoms or clinical findings and a single sign, symptom or clinical finding is linked to a number of disease or differential diagnoses. Also, these lists of diseases in books or elsewhere will also include diseases that are very rare or uncommon. If someone wants to consider all the available differential diagnoses linked to a given sign, symptom or finding during every patient encounter, the time and costs associated with such a visit would increase leading to increased health care costs, and increasing the risk of diagnostic error and creating an ineffective health care system.

There is no software available to health care providers that can process multiple signs, symptoms and clinical findings to generate a short list of high probability differential diagnoses that are clinically meaningful. Accordingly, a need exists in the art for a system and method that allows health care providers to analyze patient data and generate a high probability differential diagnoses during patient care.

BRIEF SUMMARY OF THE INVENTION

The present invention is directed to a system and method for analyzing and comparing data, such as patient data, signs, symptoms, and clinical data, and utilizing that data to generate a differential diagnoses for a particular patient to assist a health care provider in quickly generating a number of potential early hypotheses relating to a patient's condition with a reasonably high probability of being correct and providing the health care provider with various data relating to the potential condition, such as tests needed, treatment options, and severity of condition.

In one embodiment, the present invention will analyze patient conditions, signs, and symptoms and generate a differential diagnoses to assist health care providers in treating patients. The embodiment may also rank order the differential diagnoses based on various criteria considered during the diagnosis.

In one embodiment, the present invention will allow a healthcare provider to input patient data, such as signs, symptoms, and other data such as clinical findings and utilize that data to generate a high probability differential diagnosis to reduce potential errors in diagnosis usually seen in expert vs novice diagnosis of patients. In such an embodiment, an average of 2 to 6 high probability diagnoses can be presented to a health care provider for consideration in treating patients. The present invention will also utilize various data for the purpose of providing test ordering strategy and disease management strategies.

In another embodiment, the present invention can also generate a low probability differential diagnosis for the purpose of assisting health care providers in diagnosing and locating rate diseases among patients.

The present invention can help any healthcare provider to process a patient's signs/symptoms/findings (SSF) in a manner that one will be able to quickly focus on the most likely diagnoses. The present invention will also enable any mid-level health care provider, nurse practitioner or physician assistant to evaluate and process medical data in an effective fashion. Most importantly, the present invention can be an asset for the academic and training environment where medical residents and students deliver patient care, as it may help them avoid diagnostic error and avert unnecessary health care expenditure by reducing diagnostic work-up. Moreover, nurses can educate themselves about a patient's presenting diagnoses and provide important data to the physician and they can even provide diagnostic work up reminders to respective health care providers. Overall the present invention can work as a reminder system for critical diagnoses and improve patient safety.

The foregoing has outlined rather broadly the features and technical advantages of the present invention in order that the detailed description of the invention that follows may be better understood. Additional features and advantages of the invention will be described hereinafter, which form the subject of the invention. It should be appreciated that the conception and specific embodiment disclosed may be readily utilized as a basis for modifying or designing other structures for carrying out the same purposes of the present invention. It should also be realized that such equivalent constructions do not depart from the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
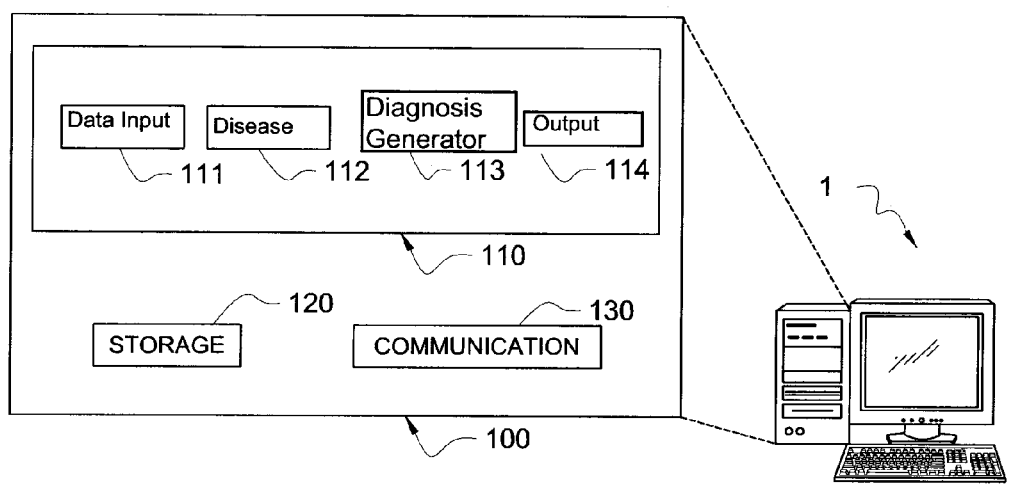
FIG. 1 is an illustration of a general architecture of a system of one embodiment of the present invention.

FIG. 1 is a diagram illustrating patient data input-disease-differential diagnoses-output environment 100 according to one embodiment of the present invention implemented on computer 1 for analyzing patient signs/symptom data to perform a differential diagnosis and generate diagnoses for a user/health care provider treating a particular patient. A health care provider, such as a physician and/or a nurse, can collect patient data and input that data to the present invention. That inputted data along with other data, such as clinical data, various disease data, and the like will be compared and analyzed by present invention so that a differential diagnosis can be output by the present invention to assist the health care provider in providing care to a patient based upon the output from the present invention. In addition to data input-disease-differential diagnoses-output environment 100, the computer system may include an operating system, a computer's coordinating program that is built on the instruction set for a processor or microprocessor, and the hardware that performs the logic operations and manages the data movement of the computer.

Data input-disease-differential-diagnoses-output environment 100 represents one application running on computer 1. In one embodiment of the present invention, data input-disease-differential diagnoses-output environment 100 includes diagnosis module 110, storage module 120, and communication module 130. Diagnosis module 110 may also include data input sub-module 111, disease sub-module 112, diagnosis generation sub-module 113 and output sub-module 114. Data input-disease-differential-diagnoses-output environment 100 is advantageous as it may be used to analyze various health care related data, such as patient signs, symptoms, and clinical data associated with a patient and then compare and analyze that data against other data, such as a disease database to generate a differential diagnosis that may be ranked in a number order based on a priority of high to low probability. This generated differential diagnosis may then be used by the health care provider to treat a patient accordingly.

Although FIG. 1 illustrates diagnosis module 110 with only four sub-modules, data input sub-module 111, disease sub-module 112, diagnosis generation sub-module 113 and output sub-module 114, the present invention is not limited to this configuration. In alternative embodiments of the present invention, diagnosis module 110 may include several other sub-modules in addition to sub-modules 111, 112, 113, and 114.

Storage module 120 enables the saving and storing of data, such as patient data, disease data, differential diagnosis data, and other related medical data. After a differential diagnosis has been generated, storage module 120 allows a user, such as a health care provider, to save the differential diagnosis and any related reports or data. Storage module 120 may also allow a user to save any specific data that is analyzed during the data analysis, and differential diagnosis generation process. For example, if the data analysis reveals a pattern of a particular differential diagnosis for a particular geographic region, patient age group, or patient gender type, a user can store various details and/or notes that can be retrieved at a later date by a user.

Communication module 130 enables a user to communicate with others and access external databases located in remote locations when in the process of analyzing data in using the present invention. In one embodiment of the present invention, this is accomplished by communication module 130 handling any data, such as retrieving various medical data that may be stored on and retrieved from an external third party database, such as databases storing clinical data, medical journals or articles or even patient data that may be stored in an external database. Communication module 130 may communicate data, such as medical data, differential diagnoses for patients, patient data or data reports to third parties, such as health care providers at different locations, by, sending an electronic message, sending an email, sending an Short Message Service (SMS) message, sending a text message, any combination of the above, and the like.

Diagnosis module 110 will query and analyze data, such as patient data that may be input by a health care provider when interviewing or meeting with a patient. In addition, diagnosis module 110 may also process all the signs, symptoms or clinical findings associate with or related to a patient and generate a short list of high probability differential diagnoses. Generation of such a list will help reduce diagnostic error and improve patient safety. Diagnosis module 110 may also act as a reminder system for health care providers and can also act to avert diagnostic error by generating the short list of high probability diagnoses. All human diseases are linked to a set of clinical signs, symptoms and clinical findings. A sign, symptom or clinical finding (SSF) may be present in multiple diseases. For example, a fever (a symptom) can be present in pneumonia, a urinary tract infection, sepsis, cellulitis, a pulmonary embolism, and many other conditions. Diagnosis module 110 may analyze the signs, symptoms, or clinical findings (SSF) related to a patient and then compare this patient data to a database of signs, symptoms or clinical findings that are linked to multiple diseases (called differential diagnoses) to ultimately provide a differential diagnosis for the health care provider. The present invention may be configured so that in includes an internal database of signs, symptoms or clinical findings or the present invention may be configured to connect to or communicate with external databases containing such information in addition to other related medical information to assist in generating a differential diagnosis.

Inputting data, such as patient data, may be accomplished via data input sub-module 111. Data sub-module 111 may function to intake and store all data input by a health care provider, such as patient data. Such patient data may include various types of data regarding a patient, such as name, date of birth, weight, height, race, gender, current medical conditions, current medications, surgery history, family medical history, current signs and symptoms, blood pressure, and the like. Any data input by a user/health care provider will be managed and handled by data sub-module 111. In one embodiment, data sub-module 111 may create a data record for all data input for a particular patient and may then store that data in a database or other storage system. Data sub-module may also be configured to provide a means for obtaining data through various means, such as user input with a keyboard or other device, use of barcodes, quick response (QR) codes, electronically scan-able or readable labels and the like.

In an embodiment of the present invention, disease sub-module 112 may operate to interface data input sub-module 111 and diagnosis generator sub-module 113 with an internal database of diseases or medical conditions and/or the signs, symptoms or clinical findings related to said diseases or medical conditions. Disease sub-module 112 may also be configured to connect to or communicate with external databases containing various medical information that can be accessed for use in generating a differential diagnosis based upon various patient data input through data input sub-module 111. In addition, the querying of data, such as medical data, from different data sources may be accomplished by disease sub-module 112. In one embodiment of the present invention, disease sub-module 112 may query data from any data source, such as databases of available medical journals, studies, diseases, statistical data, and various historical medical data that are maintained by various third party providers. The present invention is not limited to querying data from internal databases or the third party databases discussed herein as the present invention may query data from any available source now existing or which may be created in the future. In querying data from different data sources, disease sub-module 112 may search for any number of types of relevant data, such as the disease data prevalent among particular age groups, gender, or particular geographic regions, and the like.

In an embodiment of the present invention, diagnosis generation sub-module 113 will analyze patient data input via data input sub-module 111 and interface and gather disease or medical condition data from disease sub-module 112 so that a differential diagnosis may be generated. Diagnosis generation sub-module 113 may analyze patient data, such as the medical signs, symptoms and clinical findings that a patient is experiencing, and then extract and gather all potential diseases or medical conditions from disease sub-module 112 that are common among the presenting signs, symptoms, or clinical findings of the patient. In gathering the diseases associated with the patient's signs and symptoms, diagnosis generation sub-module 113 can order the diseases based upon the common signs or symptoms present in the diseases and can then generate a short list of high probability differential diagnoses or the least number of diagnoses that explain a majority of the present signs, symptoms or clinical findings. Thus, diagnosis generation sub-module 113 can provide a short list of the most likely set of diseases or medical conditions that a patient may have and then find a diagnosis or the least number of diagnoses that may explain all of or most of the present signs, also known as Ockham's razor. This short list will be called high probability differential diagnoses as they explain all the presenting signs, symptoms, or clinical findings. In generating this short list of the most likely set of diseases or conditions that a patient can have, the present invention may save health care expenditure by reducing unnecessary diagnostic work up.

Formatting and putting together reports that may be used by health care providers or users for use during patient diagnosis and treatment may be accomplished via output sub-module 114. Output sub-module 114 will handle data, such as data generated by diagnosis generator sub-module 113, and can then take that generated data and assemble, create, and output any number of reports, specific data fields, and the like that a health care provider/user may use when providing care or treatment to a patient. For example, output sub-module 114 can generate a report for a particular patient that contains individual data about a patient's medical condition and can also include on the report a listing of potential diseases and/or conditions that the patient may have based upon the diagnosis generated by diagnosis generator 113. In some embodiments, output sub-module 114 may also create disease history reports that keep track of the various disease and/or conditions that were generates as a potential patient disease or condition so that health care providers can access the data for later use including, but not limited to, keep track of various trends related to diseases or conditions. For instance, the present invention may generate and store reports in a database that allow health care providers to track the most prevalent disease or condition existing among patients of a certain age, race, and gender for a particular geographic region during a particular time or year.

The program code segments making up data input-disease-differential-diagnoses-output environment 100 can be stored in a computer readable medium or transmitted by a computer data signal embodied in a carrier wave, or a signal modulated by a carrier, over a transmission medium. The "computer readable medium" may include any medium that can store or transfer information. Examples of the computer readable medium include an electronic circuit, a semiconductor memory device, a ROM, a flash memory, and erasable ROM (EROM), a floppy diskette, a compact disk CD-ROM, an optical disk, a hard disk, a fiber optic medium, a radio frequency (RF) link, etcetera. The computer data signal that can propagate over a transmission medium such as electronic network channels, optical fibers, air, electromagnetic, RF links, etcetera. The code segments may be downloaded via computer networks such as the Internet, Intranet, and the like.

Figure 2:
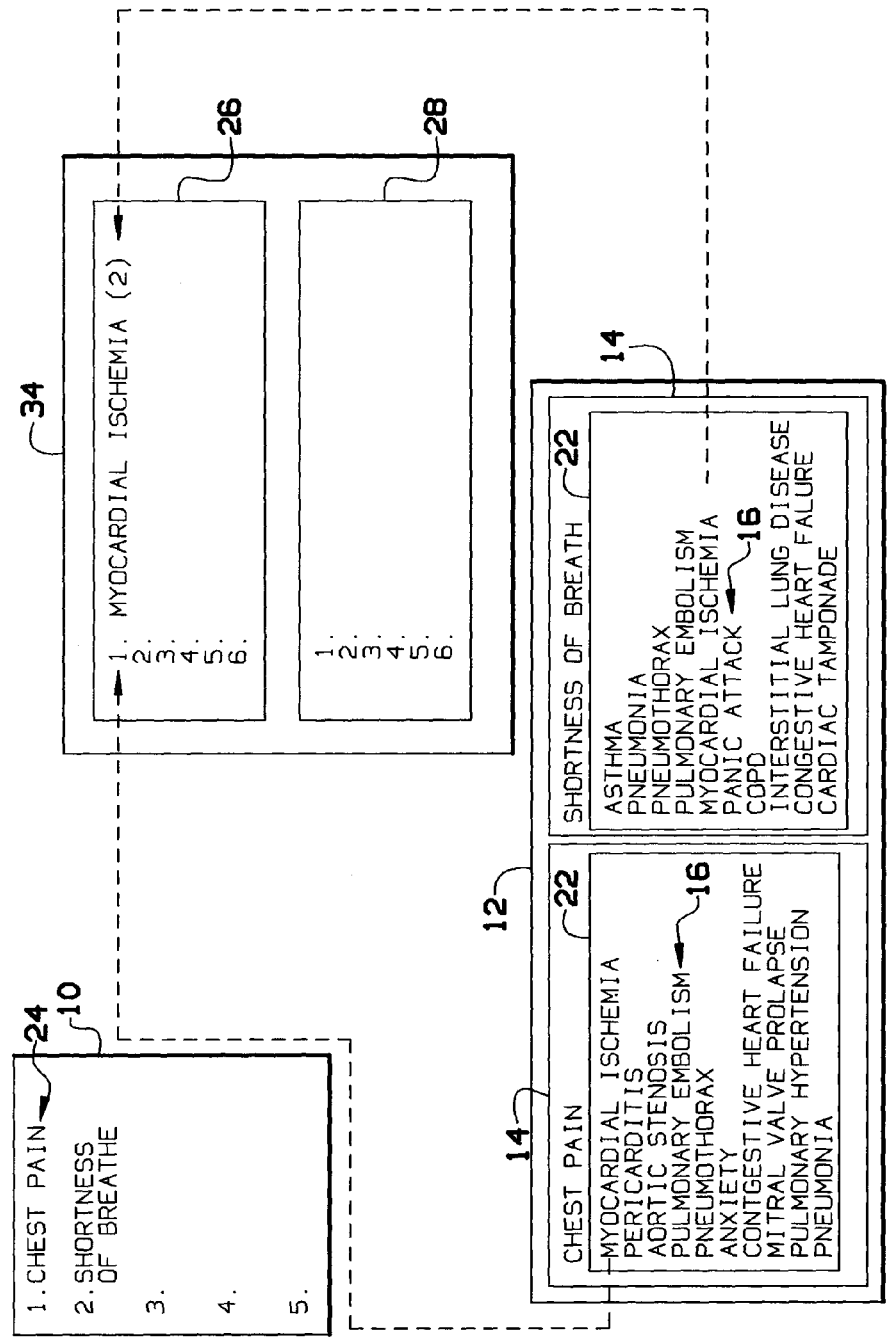
FIG. 2 illustrates a schematic exemplary view of an embodiment of the present invention.

FIG. 2 illustrates a schematic exemplary view of an embodiment of the present invention. Illustrated in FIG. 2 is input list 10 with a plurality of inputs 24. While FIG. 2 only illustrates five inputs 24, the present invention is not limited to five inputs as the present invention may have any number of inputs 24. Inputs 24 are preferably the signs/symptoms/findings that a patient is experiencing which may be inputted or selected by a user, such as a health care provider, when the heath care provider is interviewing or obtaining information from an individual/patient. Inputs 24 may consist of conditions a patient is experiencing and may also include laboratory data, radiological data, vital signs, clinical findings and the like. In one embodiment, input list 10 is created by the user/health care provider selecting or inputting inputs 24 during a patient interview or treatment. For instance, when a health care provider is interviewing a patient who is experiencing chest pain and shortness of breath, then the health care provider can input or select these symptoms 24 as illustrated in FIG. 2. In inputting or selecting symptoms/inputs 24, a health care provider will preferably input or select the symptoms 24 based upon the severity or importance of the symptoms. Thus, a health care provider in interviewing a patient will preferably input the symptoms 24 based upon his/her analysis of the patient's condition making sure to input the symptoms 24 so that the most severe or important symptom is input first followed by the next important or severe symptom 24. Thus, in FIG. 2, chest pain listed as the first symptom 24 would have been considered more severe or important than shortness of breath which is listed as the second symptom 24 in input list 10.

In the present invention, a health care provider can actually type in the inputs 24 into input list 10 or the present invention may be configured so that a user can select the input 24 from selecting from a list of signs or symptoms. The present invention may also be configured so that as a user begins to input the first letter of a sign/symptom, then all signs/symptoms beginning with that same first letter will appear so that the user can select the sign/symptom instead of having to input the entire sign/symptom.

As a user inputs or selects inputs 24 in input list 10, the present invention may operate to isolate all potential diseases or conditions associated with each specific input 24. As illustrated in FIG. 2, in isolating all potential diseases or conditions associated with each specific input 24, the present invention may create a differential diagnosis data table 12. Differential diagnosis data table 12 is simply a data table illustrating the diseases or conditions associated with each specific input 24. Differential diagnosis data table 12 may be configured to include one or more sub-tables 14. Sub-tables 14 are data tables also known as the signs/symptoms/findings (SSF)—differential diagnosis (DD) sub-table 14 or the SSF-DD sub-table 14. SSF-DD sub-table 14 is a data table that includes a symptoms table list 22 for each particular input 24. Symptoms table list 22 includes a listing of one or more potential diseases or conditions 16 or differential diagnosis (DD) 16 that are associated with the particular input 24. In a preferred embodiment, the rank order of the differential diagnosis/potential diseases DD, such as the listing of potential DD entries 16 in symptoms table list 22 will be based on epidemiological distribution (disease prevalence) of the diseases in the general population. Confirm with Azad Thus, the DD 16 in symptoms table list 22 is a potential differential diagnosis for the particular input 24. For Example, in FIG. 2, there are two inputs 24A—chest pain and 24B—shortness of breath; thus, there will be at least two SSF-DD sub-tables 14 for each particular input—one for chest pain 24A and one for shortness of breath 24B as illustrated in FIG. 2. And each SSF-DD sub-table 14 will include a symptoms table list 22 with a listing of one or more differential diagnosis (DD) 16 associated with particular inputs 24A and 24B. DD entries 16 are the actual diseases or conditions that are associated with the particular inputs 24A and 24B. Thus, the symptoms table list 22 for 24A—chest pain lists "Myocardial Ischemia" as the first DD entry 16 associated with the chest pain input 24A.

While FIG. 2 only illustrates ten DD entries 16 with each symptoms table list 22, the present invention is not limited to any particular number of DD entries 16 for any particular input 24. FIG. 2 also illustrates an output table 34 that may be output by the present invention. In one embodiment, the present invention is configured to generate output table 34 which is the actual output listing of diseases or conditions that are associated with the particular patient that is being interviewed or treated by a health care provider.

FIG. 2 also illustrates that output table 34 may include at least two lists: the ranked high probability differential diagnosis list 26 and the ranked low probability differential diagnosis list 28. Lists 26 and 28 illustrated in FIG. 2 are examples of lists that will be generated by the present invention. FIG. 2 illustrates the lists 26 and 28 before the lists have been fully populated with the potential DD entries 16.

Figure 3:
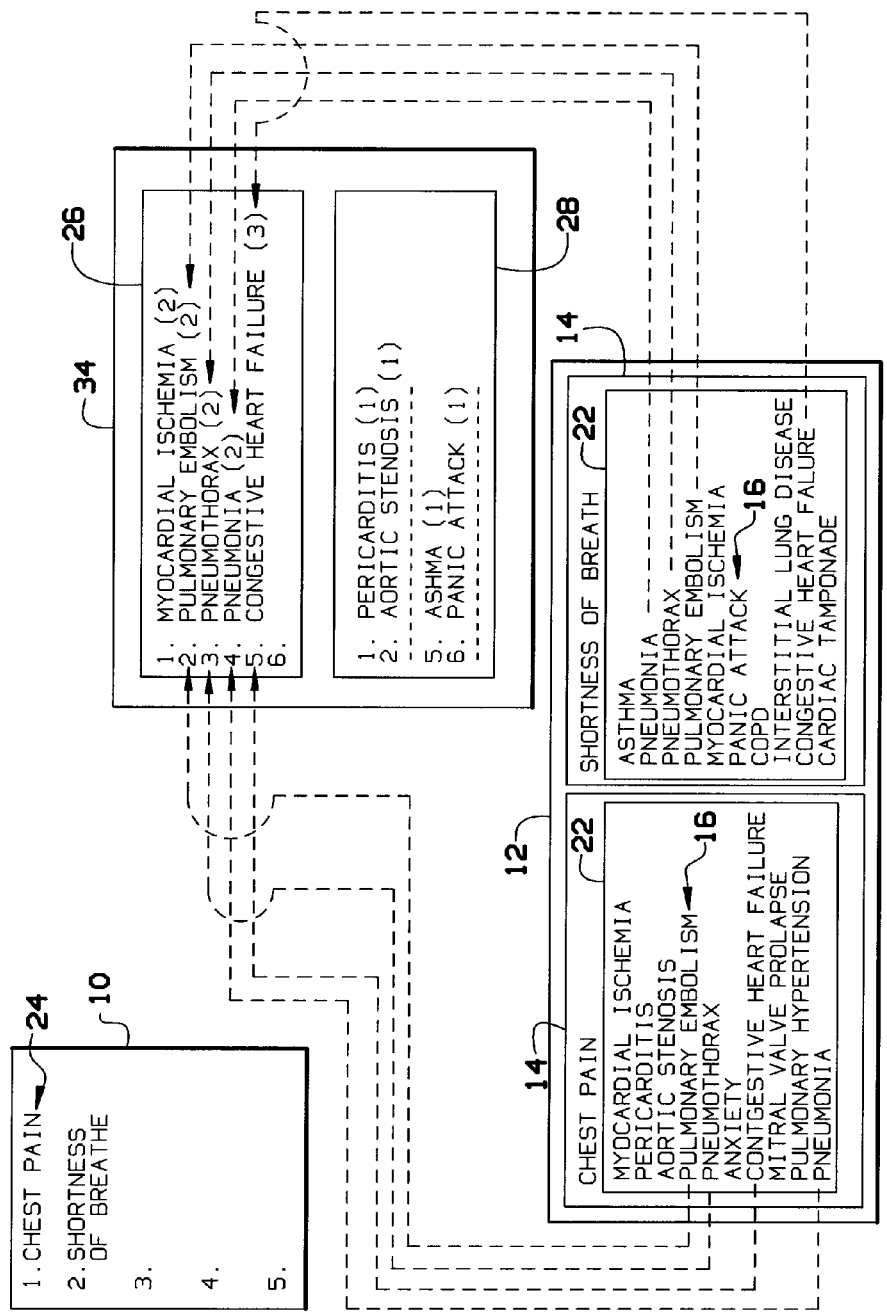
FIG. 3 illustrates another schematic exemplary view of an embodiment of the present invention demonstrating a differential diagnosis (DD) isolation.

FIG. 3 illustrates another schematic exemplary view of an embodiment of the present invention demonstrating a differential diagnosis (DD) isolation. FIG. 3 illustrates FIG. 2, but after the potential DD entries 16 have been extracted from symptoms table lists 22 and populated into the high probability differential diagnosis list 26 and the low probability differential diagnosis list 28. In FIG. 3, the high probability differential diagnosis list 26 has been populated with the potential DD entries 16 that have a high probability of being the disease or condition that a patient is suffering based upon the inputs 24 (24A—chest pain and 24B—shortness of breath) that have been input by the user/health care provider. The listing of potential DD entries 16 illustrated in lists 26 and 28 of FIG. 3 are in a non-rank sorted configuration and are merely the listing of high probability diseases for list 26 and low probability diseases for list 28. For example, list 26 would include the listing of high probability diseases associated with inputs 24A and 24B and list 28 would include the listing of low probability diseases associated with inputs 24A and 24B.

Figure 4:
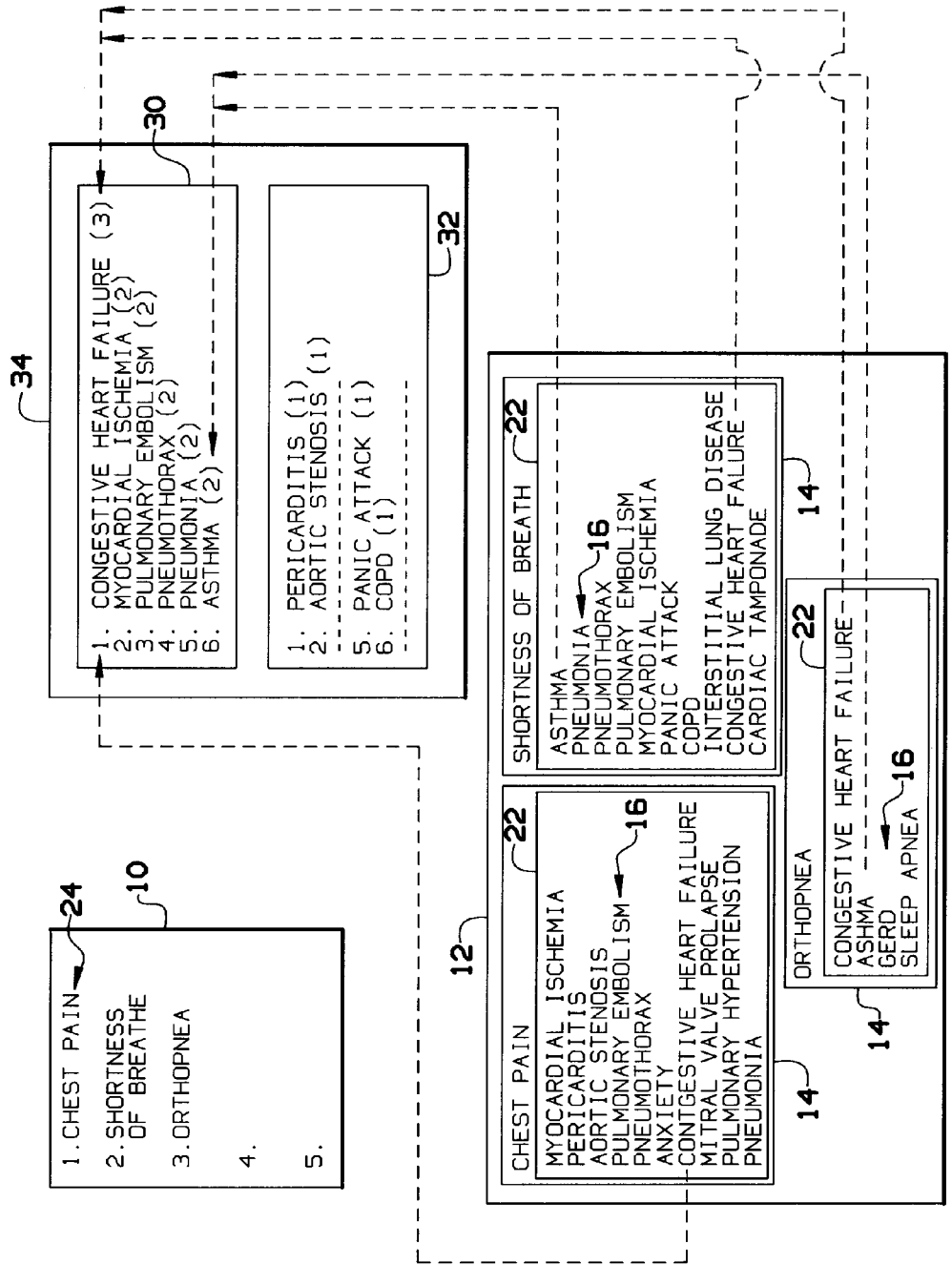
FIG. 4 illustrates is a schematic exemplary view of an embodiment of the present invention demonstrating high and low probability differential diagnosis.

FIG. 4 illustrates is a schematic exemplary view of an embodiment of the present invention demonstrating high and low probability differential diagnosis. FIG. 4 illustrates FIG. 3 after the present invention has analyzed the inputs 24, the symptoms table lists 22 and compared the symptoms tables lists 22 for the inputs 24 so that the present invention can rank the listing of high probability diseases for list 26 of FIG. 3 and rank the low probability diseases for list 28 of FIG. 3. In FIG. 4, the high probability differential diagnosis list 26 of FIG. 3 is illustrated by the ranked and sorted high probability differential diagnosis list 30. And the low probability differential diagnosis list 28 of FIG. 3 is illustrated by the ranked and sorted low probability differential diagnosis list 32. Thus, list 30 would include the ranked and sorted listing of high probability diseases associated with inputs 24A and 24B and list 32 would include the ranked and sorted listing of low probability diseases associated with inputs 24A and 24B.

In a preferred embodiment, ranked and sorted list 30 would be output to a user/health care provider to notify the health care provider of the listing of diseases that a patient has a high probability of having and also providing a user with ranked and sorted list 32 to notify the health care provider of the listing of diseases that a patient has a low probability of having.

The present invention may be configured to include a medical database of signs/symptoms/findings (SSF) and the diagnoses linked to these signs/symptoms/findings (SSF) which has been compiled from various medical resources. If a user enters any inputs 24 that are not included within such a medical database of SSF, then the new entry can be added to the medical database of SSF. Thus, a user is given the option to update the medical database in various situations, i.e. as new SSF/inputs are discovered or if a particular SSF/input is not included, and may also update the database to account for scenarios in which a particular SSF is within the database but may be listed/phrased in a particular manner that certain users may not recognize. For example, one user may list a particular input/SSF, such as "fever," as "fever" and another user may prefer to use a specific type of fever, such as "post-operative fever." If "post-operative fever" were not included within the present invention, then the user/health care provider may update the database by adding "post-operative fever" to the database. This listing/example of "fever" is for example purposes only and is not to be construed as a limitation of the present invention. In addition, due to various linguistic backgrounds, certain users/health care providers may refer to certain inputs/SSFs in one manner while users/health care providers with a different linguistic background may refer to the same inputs/SSFs in a different manner. In these situations, the users/health care providers may be given the opportunity to update the database to add inputs/SSFs to accommodate for different linguistic backgrounds. In addition, the present invention may be configured so that users/health care providers may update the diagnoses/diseases linked to the signs/symptoms/findings (SSF). For example, as new diagnoses are discovered and/or if new research were to indicate that certain signs/symptoms/findings are linked to certain diagnoses not within the medical database, then users/health care providers can update the database to contain said new diagnoses.

In one embodiment, the present invention will analyze the inputs 24 and the listing of potential DD entries 16 and further analyze which potential DD entries 16 are linked to the various inputs 24 to determine which potential DD entries 16 are common among and/or linked to the inputs 24.

By way of example, if a health care provider/user is entering and/or selecting inputs 24 which are present within the medical database of signs/symptoms/findings (SSF), the potential diseases, conditions, or differential diagnosis (DD) 16 have to be analyzed an placed in a rank order. Table 1 illustrated below illustrates potential diseases that are linked to various signs/symptoms/findings (SSF) or inputs 24 in FIGS. 2, 3, and 4. The letters utilized in Table 1 below are used for illustration purposes only whereby each letter represents a different potential disease.

TABLE 1

| Inputs/SSF | Potential Diseases/Differential Diagnoses (DD) |
| --- | --- |
| SSF1 | A, G, H, B, T, O, I, P, X, Y, Z |
| SSF2 | A, J, K, C, B, X, Q, R, S |
| SSF3 | C, U, L, N, X, T, W, V, S |

In one embodiment of the present invention, an output list of ranked and sorted high probability differential diagnosis, such as list 30 of FIG. 4 will be compiled and output based upon possible combinations of signs/symptoms/clinical and laboratory findings used in the analysis.

From Table 1, the possible combinations will include: (1) SSF1, SSF2, and SSF3; (2) SSF1 and SSF2; (3) SSF1 and SSF3; and (4) SSF2 and SSF3. An example for an analysis by an embodiment of the present invention based upon combination 1 (SSF1, SSF2, and SSF3) is as follows: a differential diagnosis (DD) (e.g., X) linked to input 3 (SSF3) is the same as the potential disease or differential diagnosis (DD) (e.g., X) linked to input 1 (SSF1) and the same as the potential disease or differential diagnosis (DD) (e.g., X) linked to input 2 (SSF2); thus, the specific potential disease or differential diagnosis DD (e.g., X) becomes ranked number one in the DD outcome section for high probability differential diagnosis because it is associated with three potential differential diagnosis (DD) and has a total weight of three associated with being linked to all three inputs (SSF1, SSF2, and SSF3). This DD (e.g., X) will be ranked ahead of other DD that are only associated with two SSF (repeated only twice). This is also based in part on the configuration in a preferred embodiment, whereby the rank order of the differential diagnosis/potential diseases DD, such as the listing of potential DD entries 16 in symptoms table list 22 is based on epidemiological distribution (disease prevalence) of the diseases in the general population.

An example for an analysis by an embodiment of the present invention based upon combination 2 (SSF1, and SSF2) is as follows: A differential diagnosis (DD) (e.g., A) linked to input 2 (SSF2) is the same as the potential disease or differential diagnosis (DD) (e.g., A) linked to input 1 (SSF1); thus, the specific potential disease or differential diagnosis DD (e.g., A) becomes ranked number two in the DD outcome section for high probability differential diagnosis (it was repeated twice). Thus, in this example, the specific disease or differential diagnosis (A) that was linked to input 1 (SSF1) and input 2 (SSF2) would be ranked number two, behind X from combination 1 in the ranked and sorted high probability differential diagnosis list 30 of FIG. 4.

A second example for an analysis by an embodiment of the present invention based upon combination 2 (SSF1, and SSF2) is as follows: A differential diagnosis (DD) (e.g., B) linked to input 2 (SSF2) is the same as the potential disease or differential diagnosis (DD) (e.g., B) linked to input 1 (SSF1). The potential disease or differential diagnosis DD (e.g., B) is located after DD (A) in the list of DD linked to input 1 (SSF1) and in the list of DD linked to input 2 (SSF2). Thus, in this example, the specific disease or differential diagnosis (B) that was linked to input 1 (SSF1) and input 2 (SSF2) would be ranked number three, behind A and X in the ranked and sorted high probability differential diagnosis list 30 of FIG. 4. This ranking is such because the present invention, in one embodiment, is configured to rank diagnoses based upon the priority in which a DD is located in the list of potential diseases or conditions, such as the listing 22 of FIGS. 2 and 3 of one or more potential diseases or conditions 16 of FIGS. 2 and 3, because the listing of potential diseases is based on epidemiological distribution (disease prevalence).

An example for an analysis by an embodiment of the present invention based upon combination 3 (SSF1 and SSF3) is as follows: A differential diagnosis (DD) (e.g., T) linked to input 1 (SSF1) is the same as the potential disease or differential diagnosis (DD) (e.g., T) for input 3 (SSF3); thus, the specific potential disease or differential diagnosis DD (e.g., T) becomes ranked number four in the DD outcome section for high probability differential diagnosis. The present invention can rank this differential diagnosis DD (e.g., T) as number four by looking at the chronology of the DD (e.g., T) linked to input 1 (SSF1). From Table 1, DDs, X, A, and B, are ranked ahead of DD (e.g., T) because X is linked to all three inputs (SSF1, SSF2, and SSF3) and is ranked first with A and B ranked second and third, leaving T to be ranked fourth.

In other embodiments, A and B will also be ranked ahead of T based upon the methodology that inputs (SSF) are selected and/or input by users/health care providers in order of severity or importance such that diseases associated with the more important input, SSF1, will be ranked ahead of diseases associated with less severe inputs, such as SSF3. By way of example, DD (e.g., A) is ranked ahead of DD (e.g., T) because DD (e.g., A) is linked to SSF1 and SSF2 while DD (e.g., T) is linked to SSF1 and SSF3. A and B are also ranked ahead of T in this particular example because both A and B are ranked ahead of T in the list of Potential diseases/ differential diagnoses linked to input 1, SSF1, illustrated in Table 1. In a preferred embodiment, the present invention will be configured so that the diagnoses/diseases in the ranked and sorted high probability differential diagnosis list, such as list 30 of FIG. 4, will be ranked based upon the order of the potential diseases/diagnoses linked to the first input (e.g., the diseases linked to SSF1) in addition to number of times a particular disease/diagnosis is also linked to other inputs (SSFs) as illustrated in the analysis herein based upon Table 1. However, when a particular potential disease/ diagnosis (e.g., A of Table 1) is found to be linked to the same number of symptoms (SSFs) as another potential disease/diagnosis (e.g., B of Table 1), then the order that the particular disease/diagnosis is ranked within the list of potential diseases/diagnoses, such as the order within symptoms table list 22 of FIGS. 2, 3, and 4, will take precedence and be ranked ahead of the other potential disease in the ranked and sorted high probability differential diagnosis list, such as list 30 of FIG. 4. Thus, A is ranked ahead of B. This ranking is premised upon the principle that the listing of diseases within the lists, such as list 22, are based upon epidemiological distribution (disease prevalence).

When the present invention performs analysis and ranking functions, if any DD stands higher in the list for input 1 (for example A stands higher than T), that specific DD takes its place as rank 1 (higher rank) as compared to the other DD (which takes its rank in the second position). Subsequently, after rankings regarding links to input 1, then rankings will be based upon links to input 2. Thus, if any DD stands higher in the list for input 2 (for example, J stands higher than K), that specific DD takes the next rank and so on.

An example for an analysis by an embodiment of the present invention based upon combination 4 (SSF2 and SSF3): A differential diagnosis (DD) (e.g., C) linked to input 3 (SSF3) is the same as the potential disease or differential diagnosis (DD) (e.g., C) for input 2 (SSF2); thus, the specific potential disease or differential diagnosis DD (e.g., C) becomes ranked number five in the DD outcome section for high probability differential diagnosis. Here priority is given to the DDs linked to input 1 (SSF1) over the DD linked to input 2 (SSF2).

The present invention may also be configured to choose between the DD that are linked to the same number of symptoms (SSFs). Again, the DDs that are linked to the greatest number of symptoms (SSFs) will be ranked ahead of those DDs that are linked to a lower number of symptoms (SSFs). For example, differential diagnosis X of Table 1 will be ranked ahead of differential diagnosis A because differential diagnosis X is linked to three symptoms (SSF1, SSF2, and SSF3) and differential diagnosis A is only linked to two symptoms (SSF1 and SSF2). Embodiments of the present invention can be configured to rank those differential diagnoses that are all linked to the same number of symptoms (SSFs) in an order amongst themselves (those DDs all linked to same number of symptoms) by reviewing and analyzing the chronology of the DDs linked to a particular input, such as input 1 (SSF1). Thus, for those DDs with an equal number or input linkings, the present invention can rank those based upon the order in which the particular DD is ranked for an input, such as input 1 (SSF1); thus, all DDs linked to two inputs (SSFs) one of which is SSF1—i.e. A, B, and T, the specific DDs that stand higher in the list of DDs linked to SSF1 will be ranked higher in the DD outcome section as compared to other DDs which stand lower in the list for input 1 (SSF1). For example, in looking at the table above, differential diagnosis/potential disease A stands in a higher position than differential diagnosis/potential disease B, and therefore differential diagnosis/potential disease A will be ranked higher than differential diagnosis/potential disease A.

In some embodiments, the present invention may also be configured to allow a user/health care provider to search records for any specific differential diagnosis or potential disease and obtain a list of all the signs, symptoms and findings that are linked to a specific differential diagnosis DD or disease. For example, utilizing Table 1, a user can search for differential diagnosis DD or potential disease A, and the present invention can provide the user with SSF1 and SSF2, which are the symptoms associated with the differential diagnosis DD or potential disease A. Providing this information will assist a user by providing a user with a system that can remind the user of the particular symptoms associated with particular inputs or signs/symptoms/findings SSFs.

Using Bayes' theorem, the maximum possible probability for any disease is 99%, not 100%. This is because the denominator of Bayes' theorem is always higher than the numerator. Thus, a maximum possible value is 0.99. So, even a probability of 99% means that 1 out of 100 patients with the exact same findings will not have the disease diagnosed, even though the presenting signs and symptoms look exactly like that disease. Thus, one should consider multiple differential diagnoses during any clinical encounter. Embodiments of the present invention will account for the possibilities that some patients will not have the disease/ diagnosis that is diagnosed as the high probability differential diagnosis. By analyzing multiple symptoms (SSFs) and providing multiple high probability differential diagnoses and also providing a listing of low probability differential diagnoses, the present invention accounts for the possibility that the patient will not have the diagnosed disease or at least one of diseases output in the lists in that the user/health care provider is provided with a list of potential diseases so that the user/health care provider can account for the fact that at least 1 out of 100 patients will not have the diagnosed disease.

According to Ockham's razor, if multiple competing theories are used to explain a fixed set of given facts, in general the theory using the least number of assumptions is given the highest credence. In diagnostic decision making, this principle means finding the fewest diagnoses that explain the most signs and symptoms. The present invention will perform its analysis of signs/symptoms/findings and compare the diseases linked to each of the signs/symptoms/findings to provide a high probability differential diagnosis output that rank orders the potential diseases that a patient may have. Thus, the present invention is configured to provide a user with the fewest diagnoses that are linked to the most signs/symptoms/findings by providing the high probability differential diagnosis output.

Health care providers may experience clinical scenarios where a unifying diagnosis (diagnosis that explains all signs, symptoms and findings) is not available. The present invention helps in that it will generate a high probability differential diagnosis output whereby most of the signs, symptoms and findings get the highest preference. According to the Bayes' theorem, it is not possible to attain 100% certainty for any given diagnosis and possibility of alternative diagnoses always exists. So it is safer to consider multiple differential diagnoses at any given time during clinical problem solving. The present invention will satisfy this rule in that embodiments of the present invention will consider all possible combinations for the available signs, symptoms and clinical findings to generate a high probability differential diagnosis. The present invention may also be configured to add up the total number of signs and symptoms that is explained by each of the differential diagnoses, and then identify the differential diagnosis that has the highest number of signs and symptoms and clinical findings for the user/health care provider so that the user/health care provider may utilize that information during the patient interview or during treatment.

The present invention may also be configured to follow epidemiologic distribution of diseases to rank order the differential diagnoses. A universal weight of 1 may be assigned to differential diagnoses linked to signs, symptoms or findings, and a higher weight may be assigned for any differential diagnoses that are life threatening, very common in a given population, and the present invention may also be configured to use age, sex, or epidemiological distribution of disease to rank order the differential diagnoses.

For example, in one embodiment, a specific weight can be assigned to each sign, symptom or finding during diagnostic decision making. In the present invention, to satisfy the rule of addition, a universal weight of one (1) is assigned to any sign and symptom or finding during generating the high priority differential diagnoses. The present invention may also be configured to use one to many relationships with signs, symptoms, or findings. In some embodiments, the present invention may be used to assign higher rank to those differential diagnoses that are common among the signs, symptoms and clinical findings. In addition, the present invention may also be configured to assign a unique name for the same disease throughout the database. Thus, the present invention may be configured to understand and utilize the simplest form of Ockham's razor and Bayes theorem in generating the high probability differential diagnosis output.

The present invention may also be configured to treat life threatening differential diagnoses differently by assigning higher weights compared to other diagnoses. Instead of assigning a universal weight of 1 for a potential disease or differential diagnosis, the present invention may assign a weight of 2 to potential life threatening diseases or differential diagnoses. In assigning the greater weights of 2, or other value, any differential diagnoses including the higher weighted life threatening diseases will take the highest place or be ranked higher in the ranked and sorted high probability differential diagnosis list 30 of FIG. 4.

In alternative embodiments, the present invention may also assign a higher weight to potential diseases or differential diagnoses that are highly prevalent in a certain group of population so that the corresponding diagnosis is ranked higher among other high probability differential diagnoses that may not be as prevalent in the certain group of population.

Some embodiments may also be configured so that rare differential diagnoses are treated differently. In particular, rare diseases may be assigned smaller weights, such as a weight value of 0.5, so that rare diseases will be ranked in the lowest of lists for such rare disease diagnoses. Thus, rare diseases may appear ranked in the bottom of the ranked and sorted low probability differential diagnosis list 32 of FIG. 4. Thus, while the rare diseases likely will not appear in the high probability differential diagnosis list, the rare diseases can be presented to a user/health care provider so that the user/health care provider will be made aware of the potential rare diseases associated with the particular signs/symptoms/findings a patient is experiencing.

The present invention will also generate low probability (less likely) differential diagnoses by accumulating all the non-repeated differential diagnoses which are linked to the sign, symptoms and findings used in the search. An embodiment may be configured to output a ranked and sorted low probability differential diagnosis list 32, as illustrated in FIG. 4. These are the diseases which are possible to present in rare situation. Thus, a user/health care provider can rule out all the available high probability differential diagnoses, and can then review the ranked and sorted low probability differential diagnosis list 32 to find a diagnosis when treating a patient.

In addition, the present invention may be configured so that users will be able to find all the signs, symptoms and findings linked to a specific differential diagnoses or disease by utilizing a reverse search strategy (instead of using signs, symptoms and findings to generate differential diagnoses, a user can search diseases to find signs, symptoms and findings). This search function will be linked to each and every differential diagnoses generated (high or low probability) to help remind and inform users of other information needed to complete a diagnostic testing or loop when evaluating a patient.

Figure 5:
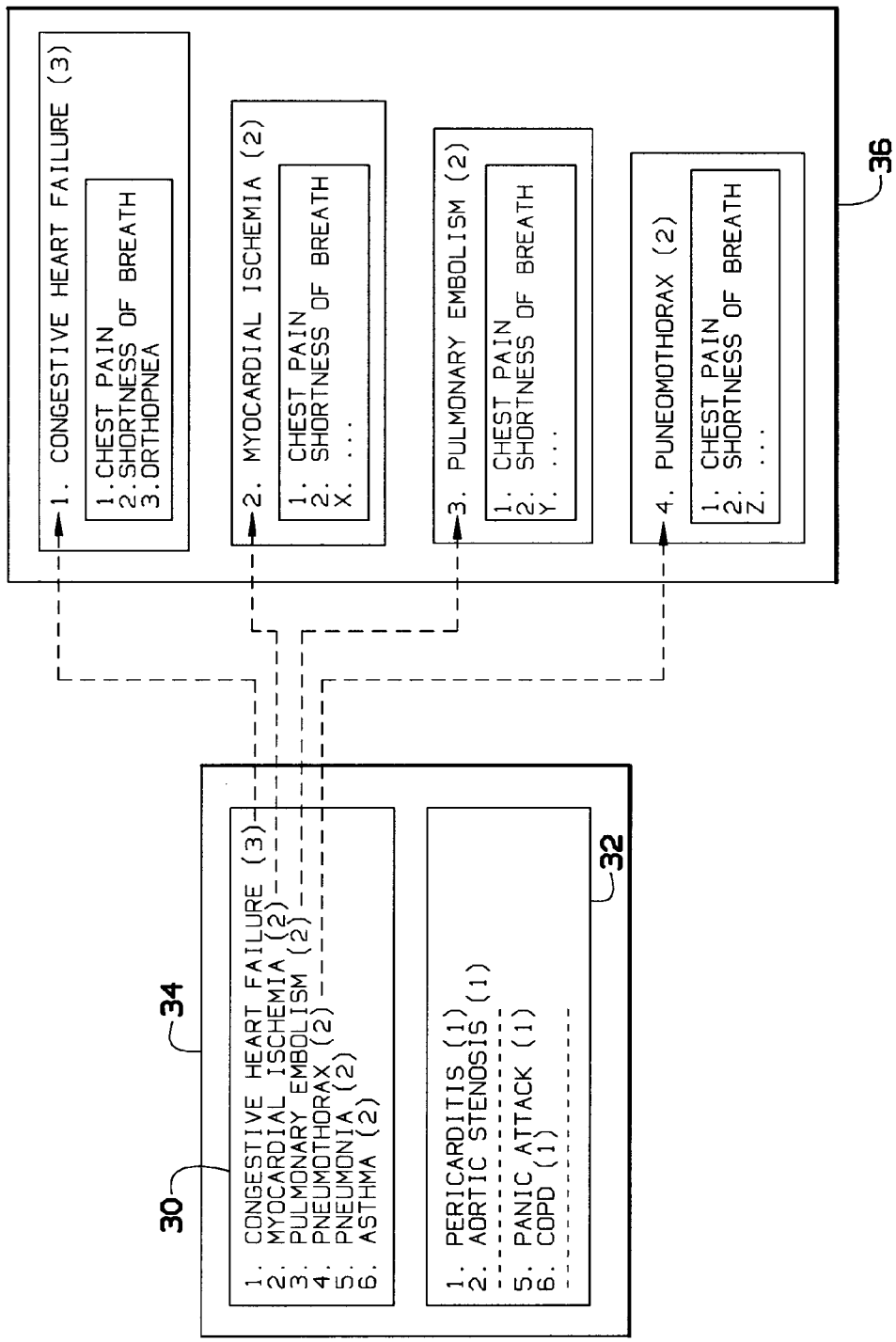
FIG. 5 is a schematic exemplary view of an embodiment of the present invention demonstrating reverse search technique where linked signs, symptoms, clinical and laboratory findings are shown.

FIG. 5 is a schematic exemplary view of an embodiment of the present invention demonstrating the reverse search technique where a user can search a disease and obtain all of the linked signs, symptoms, and laboratory findings associated with the searched disease. Illustrated in FIG. 5 is output table 34 including ranked and sorted high probability differential diagnosis list 30 and ranked and sorted low probability differential diagnosis list 32. In the present invention, a user/health care provider could search for a disease, such as congestive heart failure, as illustrated within list 30 of FIG. 5. In searching congestive heart failure, the present invention can provide a user with an illustration of the signs/symptoms/findings associated with congestive heart failure. For example, as illustrated in FIG. 5, in searching any number of diseases, such as congestive heart failure or any of the diseases illustrated in list 30 of FIG. 5, the present invention can produce a findings list 36 which lists the signs/symptoms/findings associated with the diseases that a user searched. Thus, findings list 36 illustrates the signs/symptoms/findings from the differential diagnosis data table 12 of FIG. 4. Thus, by performing a reverse search, the present invention will analyze the disease searched, such as congestive heart failure, and then provide the user with findings list 36 that lists of signs/symptoms/findings associated with congestive heart failure. In providing a reverse search capability, the present invention assists users in verifying its analysis and to assist with the patient interview in completing a diagnostic review of the patient.

In one embodiment, the present invention may also be configured to provide a user with additional information regarding the output table 34 including ranked and sorted high probability differential diagnosis list 30 and ranked and sorted low probability differential diagnosis list 32. For instance, the present invention may be configured to provide a user with other signs, symptoms and clinical findings linked to a generated differential diagnosis and provide a user with treatment strategies, disease management protocols, and other related information associated with the differential diagnoses lists, 30 and 32, contained within output table 34. Thus, once the present invention has generated a high probability differential diagnosis list of potential diseases for a patient, the user can then obtain treatment measures and strategies for treating the various diseases. These strategies may include treatment medicines, tests to be ordered, and the like.

Elements that could be added to the present invention in alternative embodiments include integrating with electronic medical records (history and physical examination, progress notes or assessments or lists of presenting signs, symptoms, clinical findings, or the like) in a fashion that could find a patient's presenting sign or symptoms, or clinical findings (by utilizing a search engine) and then generate the high probability differential diagnoses. The health care provider would be able to see reminders for those differential diagnoses during their subsequent electronic medical record review. This could work as a health care provider reminder system and might help to prevent diagnostic error.

Figure 6A:
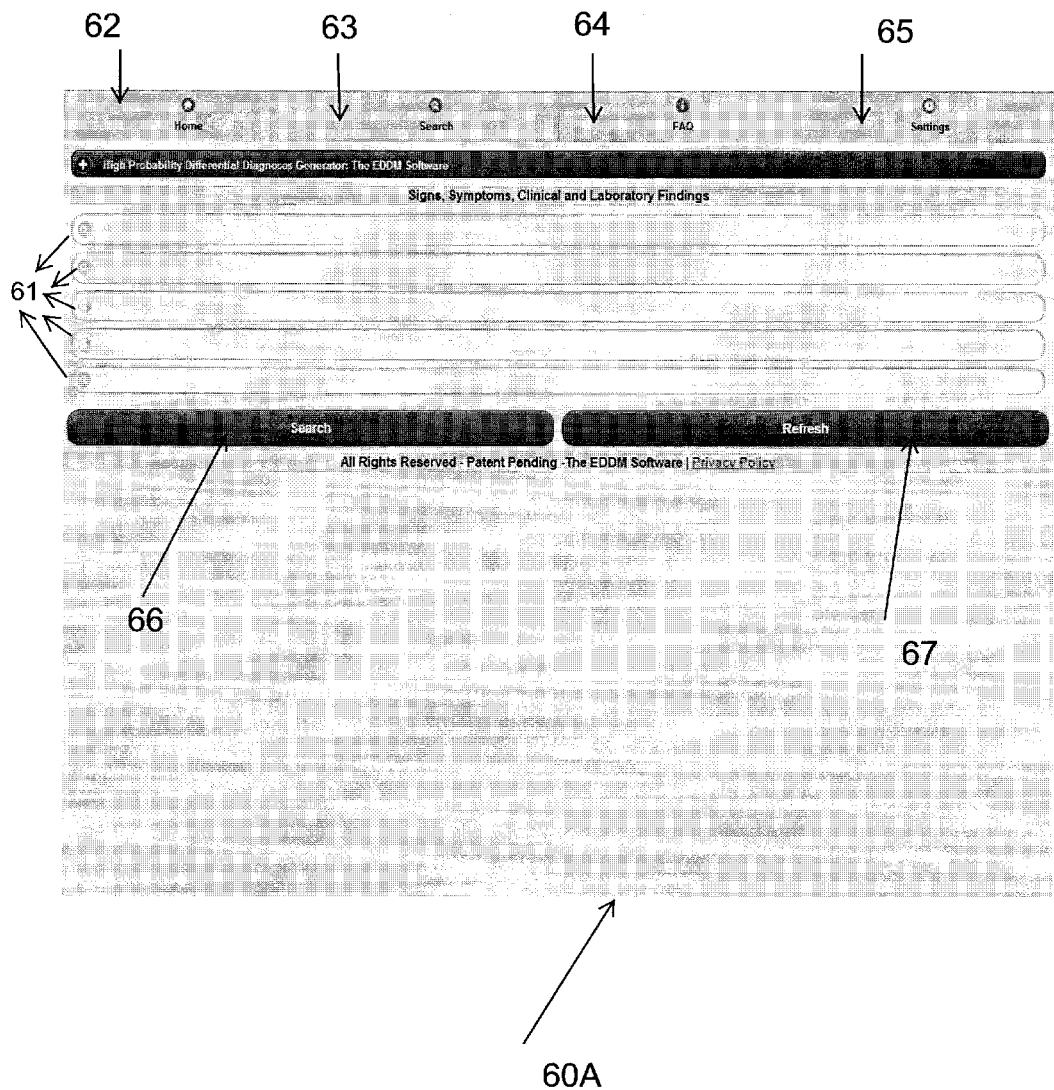
FIGS. 6A-6C illustrate screen shots of an embodiment of the present invention.
Figure 6B:
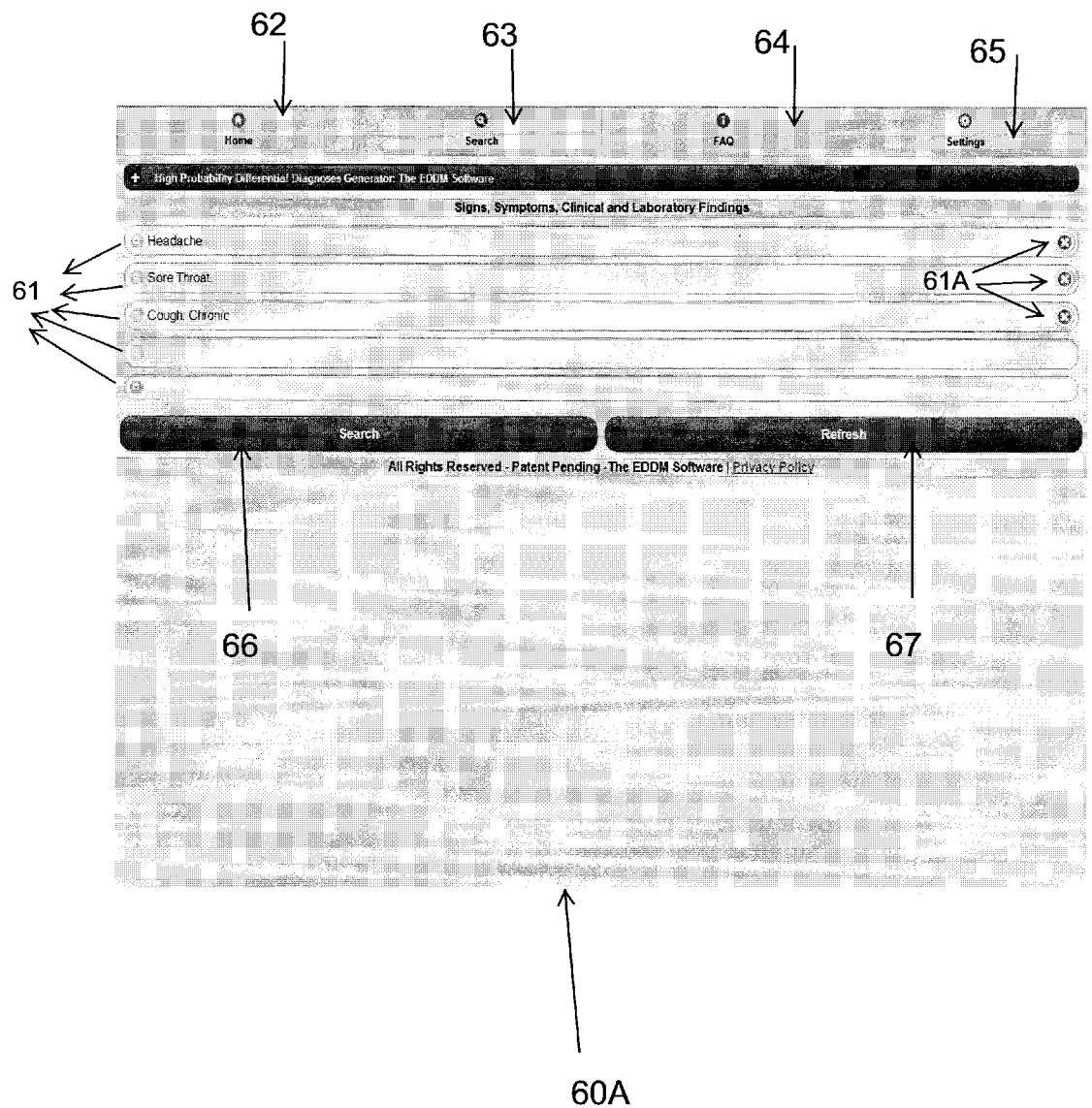
Figure 6C:
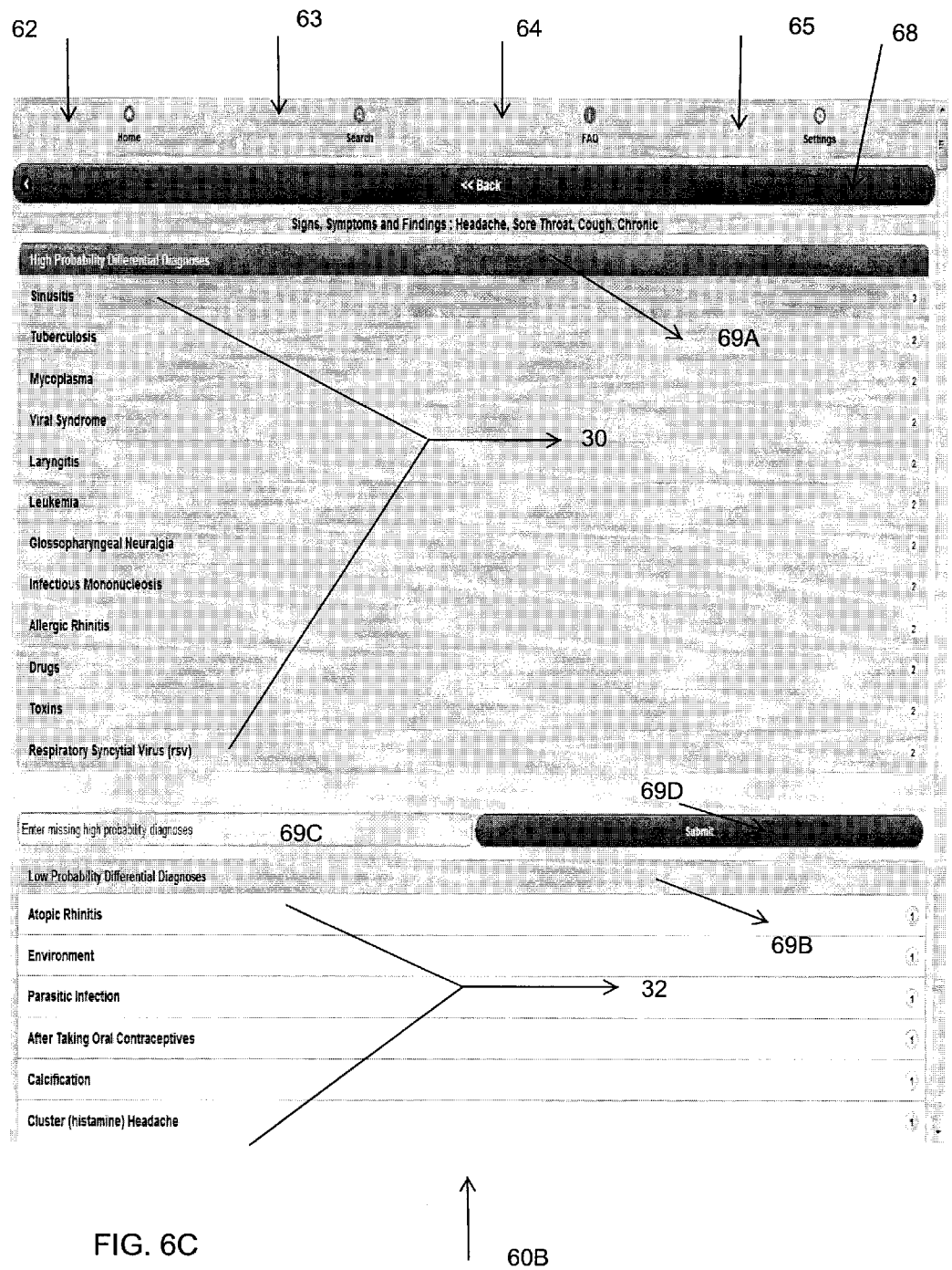

FIGS. 6A-6C illustrate sample screen shots of an example operation performed by one embodiment of the present invention. The screenshots are implemented in the EDDM™ input-disease-differential-diagnoses-output environment. It should be noted that the present invention is not limited by its application to the embodiment illustrated by EDDM™.

FIGS. 6A and 6B illustrate window 60A. Window 60A illustrates input/selection drop down boxes 61, home selector 62, search selector 63, FAQ (frequently asked questions) selector 64, settings selector 65, search selector 66, and refresh selector 67. Input/selection drop down boxes 61 provides a manner in which a user can input/select a sign/symptom/clinical finding (SSF) that a patient is experiencing from a medical database of various signs/symptoms/clinical findings, such as headache, sore throat, chronic cough, chest pain, shortness of breath, orthopnea, etcetera. The present invention is not limited to this list as any number of symptoms may be available for a user to select.

Home selector 62 is a manner in which a user can get to a Home screen or may obtain help about the present window. For example, if a new user wanted information about the software, the user could activate the home selector to obtain such information; in addition, if a user were not sure how to input/select a symptom, the user could activate the home selector to obtain access to a help screen. Search selector 63 is a manner in which a user can obtain access to a window 60A to begin a new search/analysis of symptoms. From any screen, a user may be able to activate search selector 63 and the user may be returned to a blank search screen, such as window 60A of FIG. 6A to begin a new analysis/search based upon the selection of symptoms.

FAQ (frequently asked questions) selector 64 is a manner in which a user can get to a list of frequently asked questions about the present invention. For instance, the user can activate selector 64 which can then present a new window to a user that contains a list of frequently asked questions with answers to those questions for the benefit of the user. Settings selector 65 is a manner in which a user can change various settings about the present embodiment. For instance if the user wanted to change the layout, the size of text, or to review his/her login and password or change the password, the user could activate settings selector 65 to be brought to another window so that the user could carry out these functions.

Search selector 66 is a means in which a user can activate a search for a ranked high probability differential diagnosis list and a ranked low probability differential diagnosis list based upon the various inputs that are selected/input with input/selection drop down boxes 61. A user can activate search selector 66 and the user will be directed to window 60B of FIG. 6C. Refresh selector 67 provides a manner in which a user is able to clear the list of any inputs that are selected/input with input/selection drop down boxes 61 so that user may begin a new search. The lists of functions/actions set forth herein with respect to the various selectors are illustrative and do not limit the scope of the present invention.

FIG. 6B illustrates window 60 in which a user has selected/input some inputs with input/selection drop down boxes 61. Once a user has selected some symptoms (SSF) with boxes 61, the present invention may illustrate delete selectors 61A shown for each of input/selection drop down boxes 61 in which an input has been selected or input by a user. For example, in FIG. 6B, a user has input/selected three symptoms (SSFs)—headache, sore throat, and chronic cough. The user is now give the ability to delete any of those symptoms (SSFs) by activating delete selectors 61A. Thus, if a user wanted to delete the symptom sore throat, the user can activate delete box 61A next to the box illustrating sore throat. If a user wanted to delete all of the symptoms (SSFs) selected/input by a user, then the user can activate refresh selector 67.

FIG. 6C illustrates window 60B that is displayed after a user has entered/selected symptoms (SSFs) in boxes 61 and then activated search selector 66 of window 60A. Window 60B illustrates sub-window 69A, sub-window 69B, input box 69C, and submit selector 69D. Sub-window 69A displays the list of ranked and sorted high probability differential diagnosis, such as list 30 of FIG. 4. Sub-window 69B displays the list of ranked and sorted low probability differential diagnosis, such as list 32 of FIG. 4. Thus, after a user has input/selected various signs/symptoms (SSFs) in boxes 61 and activated search selector 66, the user is provided with the high probability differential diagnoses in sub-window 69A and the low probability differential diagnoses is sub-window 69B.

Input box 69C of window 60B is a manner in which a user can input any high probability diagnoses that the user/health care provider believes is missing from the list illustrated in sub-window 69A. After a user has input an diagnoses that is believed to be missing, a user can activate submit selector 69D to update the medical database to account for the missing diagnoses that should be associated with the inputs selected/input in boxes 61. The windows and illustrations in FIGS. 6A-6C regarding EDDM™ are for illustrative purposes and the present invention is not limited by its application to the embodiment illustrated by EDDM™.

Figure 7:
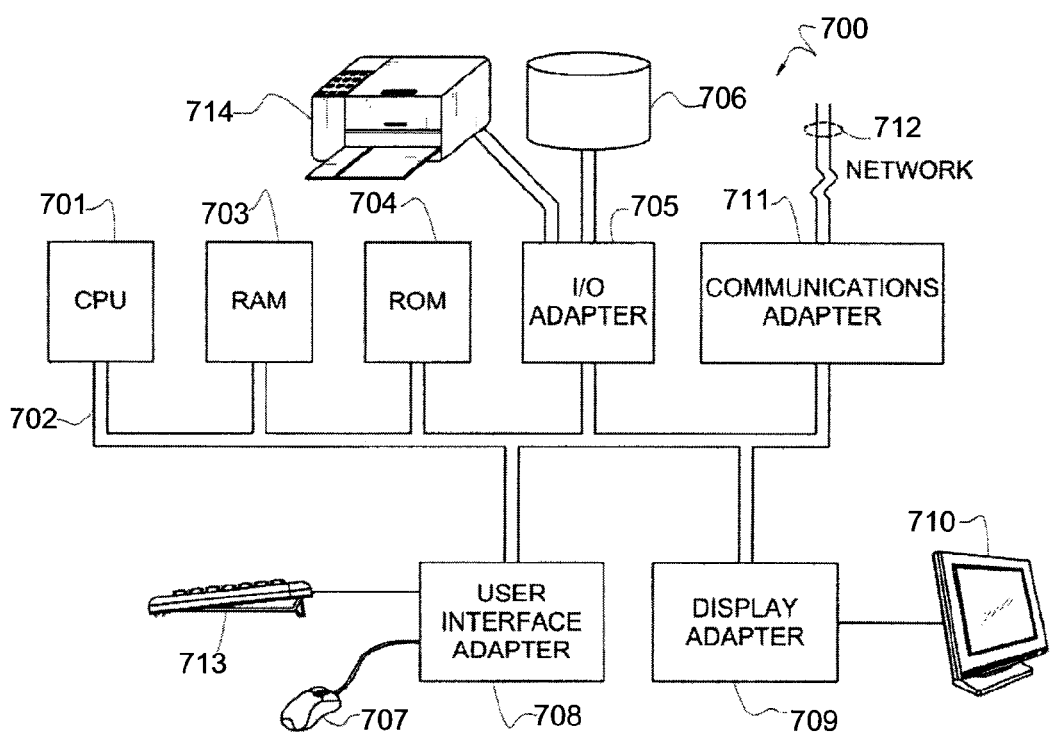
FIG. 7 depicts a block diagram of a computer system which is adapted to use an embodiment of the present invention.

FIG. 7 illustrates computer system 700 adapted to use embodiments of the present invention, e.g. storing and/or executing software associated with the embodiments. Central processing unit (CPU) 701 is coupled to system bus 702. The CPU 701 may be any general purpose CPU. However, embodiments of the present invention are not restricted by the architecture of CPU 701 as long as CPU 701 supports the inventive operations as described herein. Bus 702 is coupled to random access memory (RAM) 703, which may be SRAM, DRAM, or SDRAM. ROM 704 is also coupled to bus 702, which may be PROM, EPROM, or EEPROM. RAM 703 and ROM 704 hold user and system data and programs as is well known in the art.

Bus 702 is also coupled to input/output (I/O) controller card 705, communications adapter card 711, user interface card 708, and display card 709. The I/O adapter card 705 connects storage devices 706, such as one or more of a hard drive, a CD drive, a floppy disk drive, a tape drive, to computer system 700. The I/O adapter 705 is also connected to printer 714, which would allow the system to print paper copies of information such as documents, photographs, articles, etcetera. Note that the printer may be a printer (e.g. dot matrix, laser, etcetera.), a fax machine, scanner, or a copier machine. Communications card 711 is adapted to couple the computer system 700 to a network 712, which may be one or more of a telephone network, a local (LAN) and/or a wide-area (WAN) network, an Ethernet network, and/or the Internet network. User interface card 708 couples user input devices, such as keyboard 713, pointing device 707, etcetera to the computer system 700. The display card 709 is driven by CPU 701 to control the display on display device 710.

Although the present invention and its advantages have been described in detail, it should be understood that various changes, substitutions and alterations can be made herein without departing from the invention. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized.

What is claimed is:

1. A method for generating a high probability differential medical diagnosis comprising:
   providing a selection means whereby a first medical clinical data of a patient may be selected whereby said providing a selection means whereby a first medical clinical data of a patient may be selected comprises:
      illustrating a text box whereby a user can enter text; and
      automatically providing a selectable list of data for said user to select in response to said user entering at least one character of text into said text box;
   providing a second selection means whereby a second medical clinical data of said patient may be selected wherein said providing a second selection means whereby a second medical clinical data of said patient may be selected comprises:
      illustrating a second text box whereby a user can enter text; and
      automatically providing a second selectable list of data for said user to select in response to said user entering at least one character of text into said second text box;
   comparing said first medical clinical data and said second medical clinical data to a medical database whereby said medical database includes disease data and symptom data related to said disease data wherein said comparing said first medical clinical data and said second medical clinical data comprises:
      comparing said first medical clinical data to said medical database;
      isolating all disease data linked to said first medical clinical data;
      arranging said isolated disease data linked to said first medical clinical data into a first grouping whereby said isolated disease data is arranged in a ranked list whereby more prevalent disease data is ranked ahead of less prevalent disease data whereby more life threatening disease data within said isolated disease data is ranked higher in said ranked list linked to said first medical clinical data than less life threatening disease data within said isolated disease data;
      comparing said second medical clinical data to said medical database;
      isolating all disease data linked to said second medical clinical data; and
      arranging said isolated disease data linked to said second medical clinical data into a second grouping whereby said isolated disease data is arranged in a second ranked list whereby more prevalent disease data is ranked ahead of less prevalent disease data whereby more life threatening disease data within said isolated disease data is ranked higher in said second ranked list linked to said second medical clinical data than less life threatening disease data within said isolated disease data;
   grouping disease data from said medical database in response to said comparing wherein said grouping disease data from said medical database in response to said comparing comprises:
      comparing said first grouping of isolated disease data to said second grouping of isolated disease data; and
      isolating disease data common to said first grouping and said second grouping;
   ranking said grouped disease data;
   illustrating a listing of said ranked grouped disease data; and
   providing a third selection means whereby a third medical clinical data of a patient may be selected.

2. The method of claim 1 wherein said ranking said grouped disease data comprises:
   arranging said isolated disease data common to said first grouping and said second grouping into a ranked list whereby more prevalent disease data is ranked ahead of less prevalent disease data and more life threatening disease data is ranked ahead of less life threatening disease data.

3. The method of claim 2 wherein said illustrating a listing of said ranked disease data comprises:
   creating a graphical table of said ranked list of said isolated disease data common to said first grouping and said second grouping whereby said more prevalent disease data is illustrated higher in said graphical table than said less prevalent disease data and more life threatening disease data is illustrated higher in said graphical table than less life threatening disease data; and illustrating said graphical table.

4. A non-transitory computer readable storage medium storing a program for generating a high probability differential medical diagnosis, said program comprising:

logic for providing a selection means whereby at least a first medical symptom of a patient, a second medical symptom of a patient, and a third medical symptom of a patient may be selected wherein said logic for providing a selection means comprises:

illustrating a text box whereby a user can enter text; and automatically providing a selectable list of symptoms for said user to select in response to said user entering at least one character of text into said text box;

logic for comparing said first medical symptom to a medical database;

logic for isolating all disease data linked to said first medical symptom;

logic for arranging said isolated disease data linked to said first medical symptom into a first grouping whereby said isolated disease data is arranged in a ranked list whereby more prevalent disease data is ranked ahead of less prevalent disease data and whereby more life threatening disease data is ranked ahead of less life threatening disease data;

logic for comparing said second medical symptom to said medical database;

logic for isolating all disease data linked to said second medical symptom; and logic for arranging said isolated disease data linked to said second medical symptom into a second grouping whereby said isolated disease data is arranged in a second ranked list whereby more prevalent disease data is ranked ahead of less prevalent disease data and whereby more life threatening disease data is ranked ahead of less life threatening disease data;

logic for comparing said third medical symptom to said medical database;

logic for isolating all disease data linked to said third medical symptom; and logic for arranging said isolated disease data linked to said third medical symptom into a third grouping whereby said isolated disease data is arranged in a third ranked list whereby more prevalent disease data is ranked ahead of less prevalent disease data and whereby more life threatening disease data is ranked ahead of less life threatening disease data;

logic for comparing said first grouping of isolated disease data to said second grouping of isolated disease data and to said third grouping of isolated disease data; and logic for isolating disease data common to said first grouping, said second grouping, and said third grouping;

logic for isolating disease data common to said first grouping and said second grouping;

logic for isolating disease data common to said first grouping and said third grouping;

logic for isolating disease data common to said second grouping and said third grouping;

logic for arranging said isolated disease data into an output ranked list whereby said disease data that has been isolated as common to said first grouping, said second grouping, and said third grouping will be ranked ahead of disease data that has been isolated as common to only two of said first grouping, said second grouping, and said third grouping;

logic for arranging said isolated disease data that has been isolated as common to only two of said first grouping, said second grouping, and said third grouping into said output ranked list whereby disease data with a higher ranking in said first grouping will be ranked ahead of disease data ranked lower in said first grouping;

logic for creating a graphical table of said output ranked list;

logic for illustrating said graphical table; and logic for providing treatment data related to diseases listed within said output ranked list wherein said treatment data provides information related to the treatment of diseases contained within said output ranked list.

* * * * *